United States Patent [19]

Nastke et al.

[11] Patent Number: 5,576,009
[45] Date of Patent: Nov. 19, 1996

[54] MICROCAPSULATED PESTICIDAL FORMULATIONS, THEIR PREPARATION AND USE

[75] Inventors: Rudolf Nastke, Rehbrücke; Andreas Leonhardt, Freiburg, both of Germany; Ernst Neuenschwander, Riehen, Switzerland

[73] Assignee: Ciba-Geigy Corporation, Tarrytown, N.Y.

[21] Appl. No.: 294,181

[22] Filed: Aug. 22, 1994

Related U.S. Application Data

[63] Continuation of Ser. No. 135,372, Oct. 12, 1993, abandoned, which is a continuation of Ser. No. 941,588, Sep. 8, 1992, abandoned.

[30] Foreign Application Priority Data

Sep. 11, 1991 [CH] Switzerland ............... 2669/91

[51] Int. Cl.$^6$ ................... A01N 25/28
[52] U.S. Cl. ............. 424/408; 424/417; 424/419; 427/213.36; 264/4.33; 264/4.6
[58] Field of Search .................. 424/449, 450, 424/489, 490, 408, 409, 417, 419; 264/4.31, 4.32, 4.3; 428/402.2

[56] References Cited

U.S. PATENT DOCUMENTS

| | | | |
|---|---|---|---|
| 3,516,846 | 6/1970 | Matson | 117/36.2 |
| 3,516,941 | 6/1970 | Matson | 252/316 |
| 3,594,328 | 7/1971 | Schibler | 252/316 |
| 3,919,110 | 11/1975 | Vassilisdes | 252/316 |
| 4,157,983 | 6/1979 | Golden | 252/316 |
| 4,696,822 | 9/1987 | Matsumura | 424/490 |
| 4,889,719 | 12/1989 | Ohtsubo | 424/408 |
| 4,936,916 | 6/1990 | Shinmitsu et al. | 106/21 |
| 5,126,061 | 6/1992 | Michael | 252/86 |
| 5,160,529 | 11/1992 | Scher et al. | 71/118 |

FOREIGN PATENT DOCUMENTS

| | | |
|---|---|---|
| 0397325 | 11/1990 | European Pat. Off. . |
| 2434406 | 2/1975 | Germany . |
| 2854904 | 6/1979 | Germany . |

OTHER PUBLICATIONS

Chem Abstract, Japan JP1069385.

*Primary Examiner*—Neil S. Levy
*Attorney, Agent, or Firm*—Marla J. Mathias; William A. Teoli, Jr.; Kevin T. Mansfield

[57] ABSTRACT

A process for the preparation of microcapsules, which comprises rapidly stirring an aqueous solution of a precondensate of urea and a dialdehyde in the molar ratio of urea to dialdehyde of 1:1 to 1:2.5, into an acidified aqueous dispersion of a water-immiscible pesticide or a readily volatile water-immiscible solvent.

4 Claims, No Drawings

MICROCAPSULATED PESTICIDAL FORMULATIONS, THEIR PREPARATION AND USE

This application is a continuation of U.S. Ser. No. 08/135,372, now abandoned, filed Oct. 12, 1993, which is a continuation of U.S. Ser. No. 07/941,588, now abandoned, filed Sep. 8, 1992.

The present invention relates to a novel formulation in the form of microcapsules of per se known pesticides, to a process for the preparation of microcapsules, and to the use of said microcapsules for controlling weeds, plant diseases, insects and representatives of the order Acarina.

The preparation of pesticidal formulations by reacting urea with formaldehyde in the molar ratio of urea to formaldehyde of 1.35:1 to 1:2 in aqueous medium and subsequently stirring the precondensate into an acidified aqueous dispersion of the pesticide is disclosed in U.S. Pat. No. 3,516,846. However, the formulations prepared in accordance with the teaching of U.S. Pat. No. 3,516,846 are not discrete microcapsules, but agglomerates of sponge-like consistency having a substantially greater particle size and a markedly greater particle weight. These properties result in a high sedimentation rate of the agglomerates, which is particularly inexpedient for formulating and storing spray mixtures. In addition, the rate of release of the active ingredient, or decomposition rate of the particles, cannot be satisfactorily controlled, as—owing to the spongy structure of differing agglomerate size—the size and surface of the particles cannot be determined with exactitude. Furthermore, the use of formaldehyde is problematical for ecological, toxicological and oncological reasons.

It is therefore the object of this invention to provide a pesticidal formaldehyde-free formulation using a urea/aldehyde precondensate, the active ingredient carrier being in the form of discrete microcapsules of defined surface and particle size.

Accordingly, the invention postulates the preparation of microcapsules by stirring an aqueous solution of a precondensate of urea and a dialdehyde selected from the group consisting of glutaraldehyde, succinaldehyde, adipaldehyde, malealdehyde, malonaldehyde, 1,3-diformylcyclopentane, o-formylhydrocinnamaldehyde, phthalaldehyde and terephthalaldehyde in the molar ratio of urea to dialdehyde of 1:1 to 1:2.5, into an acidified aqueous dispersion of a water-immiscible pesticide or a readily volatile water-immiscible solvent.

The use of an aqueous dispersion of substantially nonvolatile or solid pesticides in the process of this invention results in the formation of discrete microcapsules which contain the pesticide. The use of an aqueous dispersion of a readily volatile, water-immiscible solvent leads to the formation of microcapsules which contain the readily volatile solvent. The solvent can be removed from these capsules in simple manner, conveniently by spray drying. The hollow microcapsules so obtained are admirably suitable for encapsulating liquid or low-melting pesticides. All that is required to encapsulate the pesticides is to mix the liquid pesticide with the hollow capsules. The pesticide penetrates the capsule wall and fills out the hollow capsule. The inventive process is also particularly suitable for encapsulating water-soluble pesticides which it has not been possible to encapsulate by standard methods most of which start from dispersions or emulsions of the pesticide. The invention also relates to microcapsules which are prepared by the above described process.

The invention further relates to pesticidal formulations in the form of microcapsules having a capsule wall made from a urea/dialdehyde precondensate and prepared by the above described novel process, as well as to a process for controlling weeds, plant diseases, insects and representatives of the order Acarina, which process comprises applying a pesticidally effective amount of a formulation containing the novel microcapsules to said plants, insects and representatives of the order Acarina or to the loci thereof.

A molar ratio of urea to dialdehyde of 1:1.5 to 1:2.2 is particularly advantageous for the preparation of the precondensate. The most preferred dialdehyde is glutaraldehyde.

The preparation of the precondensate is carried out under basic to weakly acid conditions, preferably in the pH range from 5.5 to 9.5, most preferably from 7 to 8. The adjustment of the pH is not critical and may typically be made with aqueous sodium hydroxide. The preparation of the precondensate can be carded out in the temperature range from 25° to 90° C., preferably from 50° to 70° C. The reaction takes place over 10 to 120 minutes, the preferred reaction time being from 30 to 60 minutes.

The precondensates are storage stable and are preferably stored at temperatures below +10° C.

Normally any water-soluble acid may be used for acidifying the aqueous dispersion. Very suitable acids are typically formic acid, acetic acid, citric acid, hydrochloric acid, sulfuric acid or phosphoric acid. It is preferred to use citric acid or hydrochloric acid. The aqueous dispersion has a pH of 1 to 6, preferably of 3 to 5.

If a pesticide is used for the aqueous dispersion, then preferably it will be a herbicide, preferably selected from the class of the ureas, sulfonyl ureas, chloroacetanilides or triazines, an insecticide or acaricide, preferably selected from the class of the thioureas, or a fungicide, preferably selected from the class of the anilinopyrimidine derivatives.

Exemplary of suitable herbicides are: piperophos, metolachlor, pretilachlor, chlortoluron, terbuthylazine, terbutryn, dimethametryn, isoproturon, atrazine, simazine, fenclorim, triasulfuron, primisulfuron, cinosulfuron and 3-(6-methoxy-4-methyl-1,3,5-triazin-2-yl)-1-[2-(3,3,3-trifluorpropyl)phenylsulfonyl]urea.

Exemplary of suitable insecticides and acaracides are bromopropylate, cypermethrin, dichlorphos, isazofos, methidathion, profenofos, diazinon, and furathiocarb and diafenthiuron.

Exemplary of suitable fungicities are metalaxyl, pyroquilon, penconazol, fenpiclonil, propiconazol, 2-phenylamino-4-methyl-6-cyclopropylpyrimidine and difenconazol.

If a readily volatile, water-immiscible solvent is used for the aqueous dispersion, then preferred solvents arc aliphatic or aromatic hydrocarbons or mixtures thereof. Particularly preferred solvents are pentane, isopentane, hexane, heptane, cyclohexane, methylcyclohexane, benzene, toluene, xylene, diethyl ether, dibutyl ether, tetrahydrofuran or white spirit.

Suitable pesticides for encapsulating in hollow capsules in the preparation of which a readily volatile, water-immiscible solvent has been used are liquid or low-melting pesticides such as the herbicides piperophos, metolachlor and pretilachlor, the insecticides and acaricides dichlorphos, phosphamidon, monocrotophos (low-melting), isazofos, methidathion (low melting), profenofos, diazinon and furathiocarb (low-melting), and the fungicides propiconazol and 2-phenylamino-4-methyl-6-cyclopropylpyrimidine.

The wall thickness of the microencapsulated pesticide is controlled by the ratio of pesticide to the amount of precondensate. The wall thickness of the hollow capsules is controlled by the ratio of the organic phase to the amount of precondensate.

The particle size of the microcapsules is governed by the particle size of the dispersed phase. The particle diameter of the dispersed phase is correlated in turn to the stirring speed. By varying the stirring speed for dispersing the dispersed phase it is thus possible to influence the particle diameter. High stirring speeds are necessary to obtain small particle diameters. The particle size can depend on the stirring speed, type of stirrer and reactor, as well as on the physicochemical conditions, and must in the individual case be determined for the respective reaction (type of stirrer, stirring volume, viscosity of the solution and the like). The rule of thumb is that the rotation speed of the stirrer will typically be 3–16, preferably 4–8 m/sec, measured at the farthest point to the axis of rotation of the stirrer. The particle diameter is normally in the range from 1 to 100 μm, the preferred range being from 1 to 50 μm.

The following non-limitative Examples illustrate the invention in more detail.

WORKING EXAMPLES

Example 1

Preparation of a Precondensate

With stirring, 60 g of urea are dissolved in 800 g (2 mol) of a 25% by weight aqueous solution of glutaraldehyde. After adjusting the pH to 7–8 with 1N aqueous sodium hydroxide, the solution is heated to 70° C. and stirred for 10–60 minutes at this temperature. The solution is thereafter cooled to room temperature.

Example 2

Preparation of a Hollow Capsule 200 ml of water, 100 ml of white spirit and 15 ml of 37% aqueous hydrochloric acid are charged to a stirred reactor and efficiently stirred with a dispersing stirrer. Then the precondensate prepared in Example 1 is added at constant stirring intensity. After 10–15 minutes, the precondensate has precipitated to form spherical particles on the surface of the dispersed liquid droplets. A suspension of microcapsules which contains white spirit is obtained. After evaporation of the solvent by suction filtration and subsequent drying, these microcapsules form hollow capsules with a diameter of 10 to 150 μm which are suitable for the sorption of liquid pesticides. If desired, the suspension can be stirred for 60–90 minutes after addition of the precondensate; but in that case the shear is correspondingly reduced.

Example 3

Microcapsules Containing Atrazine (4-ethylamino-2-chloro-6-isopropylamino-1,3,5-triazine)

In a stirred reactor, 200 ml of water, 50 g of atrazine and 100 ml of the precondensate prepared in Example 1 are intensively mixed with a stirrer. Then, at constant stirring intensity, 0.15 mol of aqueous hydrochloric acid (32% by weight) is rapidly added. The mixture is stirred for 60 minutes to give an aqueous dispersion of microcapsules which contain atrazine and which can be formulated direct or, after suction filtration, subjected to a drying process at a temperature of 130° C.

Examples 4 and 5

In accordance with the procedure of Example 2, microcapsules of comparable quality are obtained with 0.05 and 0.015 mol, respectively, of aqueous hydrochloric acid (32% by weight) instead of 0.15 mol of aqueous hydrochloric acid (32% by weight).

Example 6

Microcapsules Containing Triasulfuron 3-(6-methoxy-4-methyl-1,3,5-triazin-2-yl)-1-[2-(2-chloroethoxy)phenylsulfonyl]urea In a stirred reactor, 200 ml of water, 50 g of triasulfuron and 100 ml of the precondensate prepared in Example 1 are intensively mixed with a stirrer. Then, at constant stirring intensity, 0.05 mol of aqueous hydrochloric acid (32% by weight) is rapidly added. The mixture is stirred for 60 minutes to give an aqueous dispersion of microcapsules which contain triasulfuron and which can be formulated direct or, after suction filtration, subjected to a drying process at a temperature of 130° C.

Example 7

Microcapsules Containing 3-(6-methoxy-4-methyl-1,3,5-triazin-2-yl)-1-[2-(3-trifluoropropyl)phenylsulfonyl]urea In a stirred reactor, 200 ml of water, 50 g of 3-(6-methoxy-4-methyl- 1,3,5-triazin-2-yl)-1-[2-(3-trifluoropropyl)phenylsulfonyl]urea and 100 ml of the precondensate prepared in Example 1 are intensively mixed with a stirrer. Then, at constant stirring intensity, 0.15 mol of aqueous hydrochloric acid (32% by weight) is rapidly added. The mixture is stirred for 60 minutes to give an aqueous dispersion of microcapsules which contain 3-(6-methoxy-4-methyl- 1,3,5-triazin-2-yl)- 1-[2-(3-trifluoropropyl)phenylsulfonyl]urea and which can be formulated direct or, after suction filtration, subjected to a drying process at a temperature of 130° C.

Example 8

Microcapsules Containing 2-phenylamino-4-methyl-6-cyclopropylpyrimidine

In a stirred reactor, 200 ml of water, 50 g of 2-phenylamino-4-methyl-6-cyclopropylpyrimidine and 100 ml of the precondensate prepared in Example 1 are intensively mixed with a stirrer. Then, at constant stirring intensity, 0.15 mol of aqueous hydrochloric acid (32% by weight) is rapidly added. The mixture is stirred for 60 minutes to give an aqueous dispersion of microcapsules which contain 2-phenylamino-4-methyl-6-cyclopropylpyrimidine and which can be formulated direct or, after suction filtration, subjected to a drying process at a temperature of 130° C.

Microcapsules of urea and dialdehyde can be prepared in particularly simple manner by the process of this invention. Aside from the fact that the process is able to avoid the use of formaldehyde, a particular advantage of the novel process is that no additional dispersants are needed to prepare the microcapsules.

What is claimed is:

1. A process for the preparation of microcapsules, which comprises stirring with a stirrer, at a speed of 3 to 16 m/sec measured at the farthest point to the axis of rotation of the stirrer, an aqueous solution which is substantially free of the group consisting of formaldehyde and melamine and consisting essentially of a precondensate of urea and glutaraldehyde, in the molar ratio of urea to glutaraldehyde of 1:1 to 1:2.5, into an aqueous dispersion of a water-immiscible pesticide, said aqueous dispersion having a pH from about 1 to 6 and being substantially free of the group consisting of formaldehyde and melamine, wherein the water-immiscible pesticide is (i) a herbicide selected from the class of ureas, sulfonyl ureas, chloroacetanilides or triazines or (ii) an insecticide or acaricide selected from the class of the thioureas.

2. A process for the preparation of microcapsules filled with liquid pesticide, which comprises stirring with a stirrer, at a speed of 3 to 16 m/sec measured at the farthest point to the axis of rotation of the stirrer, an aqueous solution which is substantially free of the group consisting of formaldehyde and melamine and consisting essentially of a precondensate of urea and glutaraldehyde, in the molar ratio of urea to glutaraldehyde of 1:1 to 1:2.5, into a readily volatile water-immiscible solvent selected from the group consisting of pentane, isopentane, hexane, heptane, cyclohexane, methylcyclohexane, benzene, toluene, xylene, diethyl ether, dibutyl ether, tetrahydrofuran and white spirit and mixtures thereof, drying the microcapsules so obtained to remove the solvent, and subsequently mixing the hollow capsules with the liquid pesticide; wherein the liquid pesticide is (i) a herbicide selected from the class of ureas, sulfonyl ureas, chloroacetanilides or triazines or (ii) an insecticide or acaricide selected from the class of the thioureas.

3. A process according to claim 1, wherein the molar ratio of urea to glutaraldehyde is 1:1.5 to 1:2.2.

4. The process of claim 1, wherein the speed is 4 to 8 m/sec.

* * * * *